US005858326A

United States Patent [19]
Kisilevsky et al.

[11] Patent Number: 5,858,326
[45] Date of Patent: Jan. 12, 1999

[54] METHODS OF INCREASING AMYLOID DEPOSITION

[75] Inventors: Robert Kisilevsky; Walter Szarek; Donald Weaver, all of Kingston; Paul Fraser, Toronto; Xianqi Kong, Kingston, all of Canada

[73] Assignees: Neurochem, Inc.; Queen's University at Kingston, both of Kingston, Canada

[21] Appl. No.: 471,093

[22] Filed: Jun. 6, 1995

[51] Int. Cl.⁶ .................. A61K 31/74; A61K 31/785; A61K 31/795; A61K 47/32
[52] U.S. Cl. .................. 424/9.2; 424/78.31; 424/78.35; 435/7.8; 435/7.95; 435/7.93; 435/7.92; 530/350; 514/772.4; 800/2
[58] Field of Search .................. 800/2; 435/7.8, 435/7.95, 7.93, 7.92; 424/9.2; 530/350

[56] References Cited

U.S. PATENT DOCUMENTS

| | | |
|---|---|---|
| 4,816,416 | 3/1989 | Averback . |
| 4,919,915 | 4/1990 | Averback . |
| 5,164,295 | 11/1992 | Kisilevsky ............... 435/7.8 |
| 5,216,127 | 6/1993 | Hirai et al. . |
| 5,221,607 | 6/1993 | Cordell et al. . |
| 5,262,303 | 11/1993 | Sipe et al. . |

FOREIGN PATENT DOCUMENTS

| | | | |
|---|---|---|---|
| 94/22437 | 10/1994 | WIPO | A61K 31/185 |
| 94/22885 | 10/1994 | WIPO | C07H 11/00 |

OTHER PUBLICATIONS

Kisilevsky et al., Critical Reviews in Clinical Laboratory Sciences, vol. 29:1, pp. 59–82, 1992.

Snow et al., Neuron, vol. 12: 1, pp. 219–234, 1994.

Glombitza, K.W., et al., "Phenolsulphate esters from Phaeophyceae", *Bull. Liaison–Groupe Polyphenols.* vol. 14, pp. 244–247 (1988).

Ragan, M., "Phenol sulfate esters: ultraviolet, infrared, $^1$H and $^{13}$C nuclear magnetic resonance spectroscopic investigation", *Can. J. Chem.* vol. 56, No. 20, pp. 2681–2685 (1978).

Ragan, M., et al. "Paired–Ion Reversed–Phase High–Performance Liquid Chromatography of Phenol Sulfater in Synthetic Mixtures, Algal Extracts and Urine", *Journal of Chromatography,* vol. 178, pp. 505–513 (1979).

International Search Report dated Oct. 18, 1996.

Kirschner, D.A., et al., "Synthetic peptide homologous to β protein from Alzheimer disease forms amyloid–like fibrils in vitro", *Proc. Natl. Acad. Sci USA* 84: 6953–6957 1987.

Castaño, E.M., et al, "In Vitro Formation of Amyloid Fibrils from Two Synthetic Peptides of Different Lengths Homologous to Alzheimer's Disease β–Protein", *Biochemical and Biophysical Research Communications* 141:782–789 (1986).

Gruys, E., et al, "Animal models for reactive amyloidosis", *Bailliére's Clinical Rheumatology* 8: 599–611 (1994).

Gorevic, P.D., et al., "Ten to Fourteen Residue Peptides of Alzheimer's Disease Protein are Sufficient for Amyloid Fibril Formation and its Characteristic Xray Diffraction Pattern", *Biochemical and Biophysical Research Communications* 147:854–862 (1987).

WHO–IUIS Nomenclature Sub–Committee, "Nomenclature of amyloidosis", *Bulletin of the World Health Organization* 71:105–108 (1993).

Connors, L.H., et al., "In Vitro Formation of Amyloid Fibrils from Intact $\sigma_2$ Microglobulin", *Biochemical and Biophysical Research Communications* 3: 1063–1068 (1985).

Magnus, J.H., et al., "Proteoglycans, glycosaminoglycans and amyloid deposition", *Bailliére's Clinical Rheumatology* 8: 575–597 (1994).

Nitta A., et al, "β–Amyloid protein–induced Alzheimer's disease animal model", *Neuroscience letters* 170: 63–66 (1994).

Li, X.A., et al., "Binding of serum amyloid P component heparin in human serum", *Biochimica et Biophysica Acta* 1201: 143–148 (1994).

Schwarzman, A.L., et al. "Transthyretin sequesters amyloid β–protein and prevents amyloid formation", *Proc. Natl. Acad. Sci. USA* 91: 8638–8372 (1994).

Merlini, G., "Treatment of Primary Amyloidosis" *Seminars in Hematology* 32: 60–79 (1995).

Glenner, G.G., et al., "Creation of 'Amyloid' Fibrils from Bence Jones Proteins in vitro", *National Institutes of Health* 174: (Nov. 1971).

Caughey, B., et al., "Scrapie–associated PrP Accumulation and Its Inhibition: Revisiting the Amyloid–Glycosaminoglycan Connection", *Annals New York Academy of Sciences* 290–295.

*Primary Examiner*—Jasemine C. Chambers
*Assistant Examiner*—Jill D. Schmuck
*Attorney, Agent, or Firm*—Giulio A. DeConti, Jr.; Elizabeth A. Hanley; Lahive & Cockfield, LLP

[57] ABSTRACT

In vivo and in vitro methods of increasing amyloid deposition using amyloid-enhancing compounds are described. Methods of forming amyloid fibrils and screening for agents useful in treating amyloidosis are also described. Animals having non-naturally occurring amyloid deposits produced using the amyloid-enhancing compounds even further are described.

5 Claims, 2 Drawing Sheets

METHODS OF INCREASING AMYLOID DEPOSITION

BACKGROUND OF THE INVENTION

Amyloidosis refers to a pathological condition characterized by the presence of amyloid. Amyloid is a generic term referring to a group of diverse but specific extracellular protein deposits which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common x-ray diffraction and infrared spectra.

Amyloid can be classified according to the protein type, as described in a recent report (Kazatchkine et al., (1993) *Bull. WHO* 71:105). Different amyloidoses are also characterized by the type of protein present in the deposit. For example, neurodegenerative diseases such as scrapie, bovine spongiform encephalitis, Creutzfeldt-Jakob disease and the like are characterized by the appearance and accumulation of a protease-resistant form of a prion protein (referred to as AScr or PrP-27) in the central nervous system. Similarly, Alzheimer's disease, another neurodegenerative disorder, is characterized by congophilic angiopathy, neuritic plaques and neurofibrillary tangles, all of which have the characteristics of amyloids. In this case, the plaques and blood vessel amyloid is formed by the beta protein. In other systemic diseases such as adult-onset diabetes, the protein is amylin, in complications of long-term hemodialysis, the protein is beta-2-microglobulin, in sequelae of long-standing inflammation, the protein is serum amyloid A (SAA), and in plasma cell dyscrasias, amyloids are characterized by the accumulation of light chains systemically. In each of these cases, a different amyloidogenic protein is involved in amyloid deposition.

Once these amyloids have formed there is no generally accepted therapy or treatment to dissolve the deposits in situ. There is, therefore, an urgent need for therapeutic agents which can either inhibit the formation or growth of amyloid or dissolve amyloid deposits once formed. Co-pending U.S. patent application Ser. No. 08/403,230 describes methods and compositions of sulfated and sulfonated compounds, or functional equivalents thereof, useful in the treatment of amyloidosis in vivo.

One difficulty encountered in identification of therapeutic agents for the treatment of amyloidosis is the lack of rapid, general screening assays for such agents. U.S. Pat. No. 5,164,295 describes a screening assay which measures the ability of a compound to inhibit the interaction between an amyloid protein and an extracellular matrix protein. U.S. Pat. No. 5,348,963 describes an assay which screens compounds based on their ability to alter the intracellular processing of amyloid precursor proteins in mammalian cells in cell culture. Co-pending U.S. patent application Ser. No. 08/403,230 describes a mouse model of amyloidosis which is used for screening for compounds which have the ability to decrease amyloid formation in vivo.

Another difficulty encountered in searching for treatments for amyloidosis is that the mechanism of amyloid fibril formation, although extensively studied in vivo (see, e.g., R. Kisilevsky and I. Young (1994) in G. Husby, ed. "Clinical Rheumatology: Vol. 8, No. 3, Reactive Amyloidosis and the Acute Phase Response" London: Bailliere Tindall, pp. 613–626; E. Gruys and F. W. J. J. Snel (1994) in Husby, ed., op. cit., pp.599–611) and in vitro (see, e.g., G. G. Glenner et al., (1971) *Science* 174:712; E. M. Castano et al. (1986) *Biochem. Biophys. Res. Commun.* 141:782; D. A. Kirschner et al. (1987) *Proc Natl. Acad. Sci. USA* 84:6953), has not been completely elucidated. In general, in vitro conditions used to cause amyloid fibril formation have not been similar to physiological conditions. The in vitro methods known in the art usually require high amyloid protein concentrations, unnatural pH ranges, or strong solvents to cause amyloid fibril formation ( see, e.g., I. B. Kingston et al., (1995) *Nature Med.*, 1:138-142; Glenner et al, (1971) op. cit.). Thus, the amyloid fibrils formed by these methods may not reflect the structure of fibrils formed in vivo, and the conclusions drawn from structural studies of such in vitro-formed fibrils may not be applicable to fibrils formed by amyloidogenic conditions in vivo.

SUMMARY OF THE INVENTION

This invention is based, at least in part, on the discovery of amyloid-enhancing compounds which are capable of increasing the rate of amyloid formation both in vivo and in vitro. The invention pertains to methods useful in increasing amyloid formation in an animal. The methods of the invention find use in animal models of amyloidosis because the induction time or formation time of amyloid formation in the animal models can be decreased. The invention also pertains to methods of inducing amyloid fibril formation in vitro.

In one aspect, the invention features a method of increasing amyloid deposition in a mammal. The method comprises administering to the mammal an effective amount of an amyloid-enhancing compound. In preferred embodiments, the amyloid-enhancing compound is a sulfonated aliphatic or aromatic compound. In a more preferred embodiment, the amyloid-inducing compound has an aromatic moiety comprising at least two sulfonate moieties. Preferred amyloid-enhancing compounds include 2-sulfobenzoic acid, benzene-1,2-disulfonic acid, benzene-1,3-disulfonic acid, benzene-1,4-disulfonic acid, or pharmaceutically acceptable salts thereof. Particularly preferred amyloid-enhancing compounds include 4,5-dihydroxy-1,3-benzenedisulfonic acid, 2,5-dihydroxy-1,4-benzenedisulfonic acid, 2,5-dimethoxy-1,4-benzenedisulfonic acid, and their pharmaceutically acceptable salts. The compounds of the invention are administered to a subject by a route which is effective for enhancement of amyloid deposition. Suitable routes of administration include subcutaneous, intravenous and intraperitoneal injection. The compounds of the invention have been found to be effective at enhancing amyloid deposition when administered orally. Accordingly, a preferred route of administration is oral administration. The compounds can be administered with a pharmaceutically acceptable vehicle.

In another aspect, the invention features a method of forming amyloid fibrils from an amyloidogenic peptide. The method features contacting an amyloidogenic peptide with an effective amount of an amyloid-enhancing compound forming amyloid fibrils.

In still another aspect the invention features a method of screening for agents useful for treating amyloidosis. The method comprises providing a reaction mixture which includes a solution of an amyloidogenic peptide, an amyloid-enhancing compound, and an agent potentially useful for treating amyloidosis, under conditions such that, in the absence of the agent potentially useful for treating amyloidosis, amyloid fibrils would form, and observing formation or absence of amyloid fibrils.

In yet another aspect, the invention provides an animal having non-naturally occurring amyloid deposits. The animal is treated with an effective amount of an amyloid-enhancing compound such that the animal has non-naturally occurring amyloid deposits.

DETAILED DESCRIPTION

Figure 1:
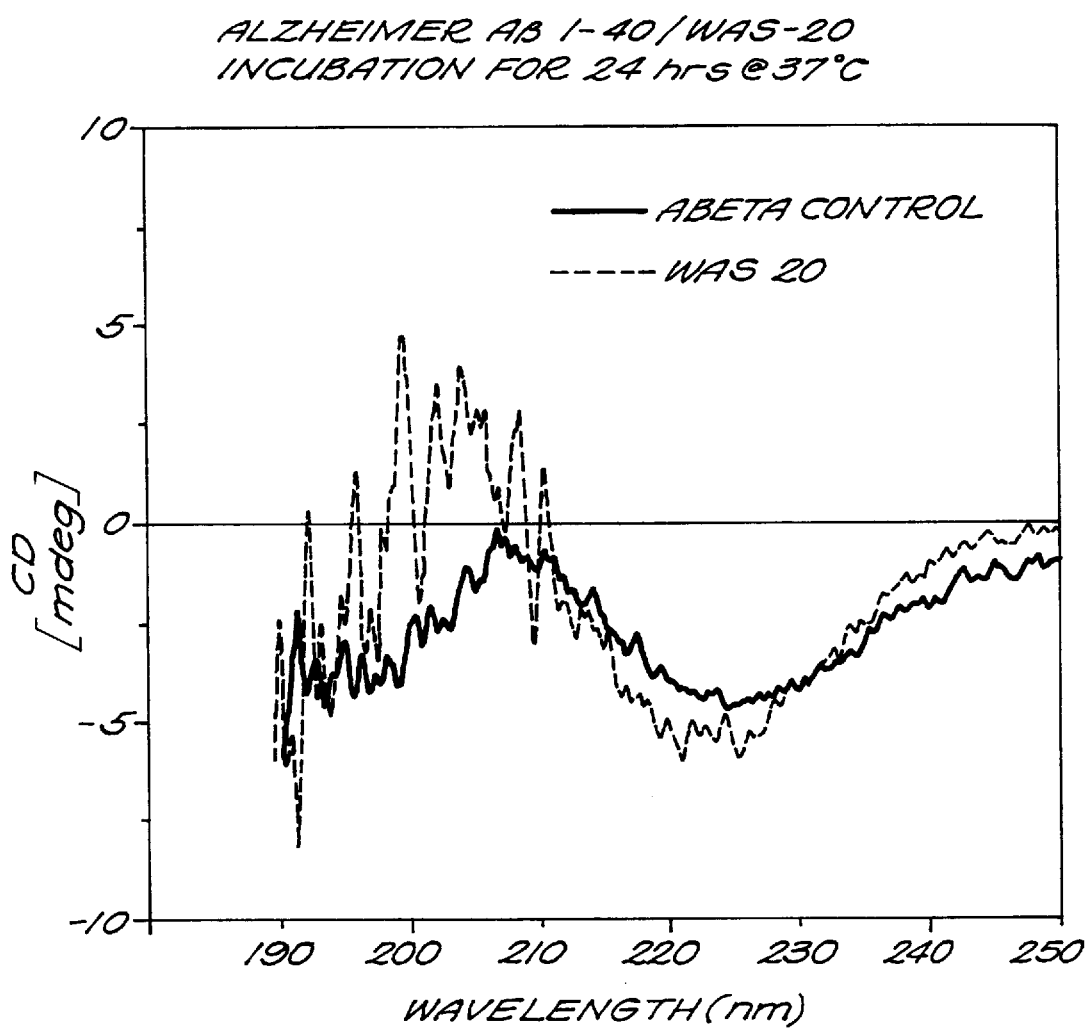
FIG. 1 shows circular dichroism (CD) spectra of Aβ in the absence and presence of WAS-20 (2,5-dihydroxy-1,4-benzenedisulfonic acid).

This invention pertains to methods useful in increasing amyloid formation in an animal. These methods of the invention find use in animal models of amyloidosis. The invention also pertains to methods of inducing amyloid fibril formation in vitro. The in vitro methods of the invention find application in the study of amyloidogenesis and amyloid fibril structure.

For convenience, certain terms used throughout the specification and appended claims are first defined.

The term "amyloid-enhancing compound", as used herein, means a compound which is capable of enhancing the rate or amount of amyloid deposition in vivo or in vitro. A compound can be tested to determine whether it is an amyloid-enhancing compound according to the methods described in the Exemplification, infra. Preferred amyloid-enhancing compounds for use in vivo do not exhibit significant toxicity when administered to an animal at levels sufficient to increase amyloid deposition in vivo. Preferred amyloid-enhancing compounds for use in vivo, when tested in the mouse model described in Example 1, infra, increase the rate or amount of amyloid deposited in mouse spleen by at least about 10 percent, more preferably at least about 20 percent, and still more preferably at least about 30 percent compared to control. It will be understood that increases in amyloid deposition can occur at certain dosages or concentrations of an amyloid-enhancing compound, but not at other concentrations or dosages. In light of the teaching herein (see, e.g., Example 1), the skilled artisan will be able to determine suitable dosages or concentrations with no more than routine experimentation. Preferred amyloid-enhancing compounds include compounds which have an aromatic moiety and at least two anionic moieties, e.g. attached to the aromatic moiety. Examples of preferred amyloid-enhancing compounds include 2-sulfobenzoic acid, 1,2-benzene-disulfonic acid, 1,3-benzene-disulfonic acid, 1,4-benzene-disulfonic acid, and their pharmaceutically acceptable salts. Particularly preferred amyloid enhancing compounds include 4,5-dihydroxy-1,3-benzene-disulfonic acid, 2,5-dihydroxy-1,4-benzenedisulfonic acid, 2,5-dimethoxy-1,4-benzenedisulfonic acid, and their pharmaceutically acceptable salts.

The terms "amyloidogenic peptide" or "amyloidogenic protein", as used herein, refer to peptides which are capable of forming amyloid deposits. Amyloids have been categorized by the type of amyloidogenic protein contained within the amyloid. Non-limiting examples of amyloids, and their amyloidogenic proteins, are as follows (with the associated disease in parentheses after the amyloidogenic protein): β-amyloid (Aβ) (Alzheimer's disease, Down's syndrome, hereditary cerebral hemorrhage amyloidosis [Dutch]); amyloid A (AA) (reactive [secondary] amyloidosis, familial Mediterranean Fever, familial amyloid nephropathy with urticaria and deafness [Muckle-Wells syndrome]); amyloid κ L-chain or amyloid λ L-chain (idiopathic [primary], myeloma or macroglobulinemia-associated); Aβ2M (chronic hemodialysis); transthyretin amyloid (TTR) (familial amyloid polyneuropathy [Portuguese, Japanese, Swedish], familial amyloid cardiomyopathy [Danish], isolated cardiac amyloid, systemic senile amyloidosis); AIAPP or amylin (adult onset diabetes, insulinoma); atrial naturetic factor (isolated atrial amyloid); procalcitonin (medullary carcinoma of the thyroid); gelsolin (familial amyloidosis [Finnish]); cystatin C (hereditary cerebral hemorrhage with amyloidosis [Icelandic]); AApoA-I (familial amyloidotic polyneuropathy [Iowa]); AApoA-II (accelerated senescence in mice); fibrinogen-associated amyloid; lysozyme-associated amyloid; and AScr or PrP-27 (Scrapie, Creutzfeldt-Jakob disease, Gerstmann-Straussler-Scheinker syndrome, bovine spongiform encephalitis). It will be understood that other natural or non-natural proteins or peptides which are capable of forming amyloid or amyloid-like fibrils in vivo or in vitro are also considered to be amyloidogenic peptides for the purposes of the present invention. For example, certain fragments of amyloidogenic peptides can form amyloid fibrils (see, e.g., P. D. Gorevic et al., (1986) *Biochem. Biophys. Res. Commun.* 147:854) and thus are considered to be amyloidogenic peptides for the purposes of the present invention.

The term "an animal having non-naturally occurring amyloid deposits", as used herein, refers to an animal which has deposits of amyloid which do not normally occur in that animal under natural conditions, and which are in excess of the amyloid deposits which occur when the animal is treated with an inflammatory stimulus and amyloid enhancing factor (AEF) (see, e.g. R. Kisilevsky and L. Boudreau, (1983) *Lab. Invest.*, 48, 53–59). For example, Swiss white mice do not normally suffer from amyloid deposits, but Swiss white mice treated with the amyloid-enhancing compounds of the present invention have enhanced amyloid deposition compared to control animals (see Example 1).

The term "anionic group", as used herein, refers to a moiety which has a net negative charge. In preferred embodiments, the anioic group has a negative charge at physiological pH. Exemplary anionic groups include sulfonate, sulfate, carboxylate, phosphate, phosphonate, and the like. Preferred anionic groups include carboxylate and sulfur containing moieties (e.g., sulfonate, sulfate and the like).

In one aspect, the invention features a method for increasing amyloid deposition in an animal. Animals which exhibit amyloidosis are useful in screening assays for compounds which inhibit amyloidosis in vivo, as described in R. Kisilevsky et al., (1995) *Nature Med.* 1:143-148, and in copending U.S. patent application Ser. No. 08/403,230, the disclosures of both of which are hereby incorporated by reference. Amyloidosis is induced in mice by treating the animal with an inflammatory stimulus, in combination with amyloid enhancing factor (AEF), as described in Kisilevsky and Boudreau, (1983) op. cit. (see Example 1). To induce long-lasting amyloidosis, repeated injections of the inflammatory stimulus are often required. Furthermore, in some animal models of amyloidosis, long periods of time must elapse between administration of an amyloid-inducing stimulus and the deposition of amyloid (Kisilevsky and Boudreau, ibid.).

The methods of the present invention make possible the development of amyloid deposits in animals in a shorter period of time and/or result in an increase in amyloid deposits over a selected period of time when compared to a control. This makes possible more rapid screening of compounds in animal models of amyloidosis (for example, the mouse model described herein). Such rapid screening is particularly desirable when large numbers of candidate compounds are to be tested, as, for example, when structure-activity relationships are being probed, or when searching for compounds for further modification. Moreover, the increased amount of amyloid deposition seen in animals treated with amyloid-enhancing compounds may result in increased sensitivity of assays for compounds effective in the treatment of amyloidosis. Compounds which have a relatively modest effect on amyloid deposition in vivo may nevertheless be useful therapeutically, or may provide important structure-activity information.

The mechanism by which the amyloid-enhancing compounds described herein increase amyloid deposition in vivo is not precisely known. It is known, however, that sulfated and sulfonated compounds effective for the treatment of amyloidosis in vivo (i.e., compounds that decrease amyloid deposition) inhibit an interaction between an amyloidogenic protein and a constituent of basement membrane, and thereby inhibit amyloid deposition (see, e.g., U.S. patent application Ser. No. 08/403,230 and references cited therein). The constituent of basement membrane is a glycoprotein or proteoglycan, preferably heparan sulfate proteoglycan (HSPG). Without being bound by theory, it is believed that the amyloid-enhancing compounds described herein enhance interactions either between an amyloidogenic protein and a component of basement membrane, or between monomers of the amyloidogenic protein, and thereby enhance amyloid deposition in vivo.

The methods of the invention also provide increased amyloid deposition in vitro. The mechanism by which the amyloid-enhancing compounds described herein increase amyloid deposition in vitro is also not precisely known.

The above-described mouse model of amyloidosis is a useful model of amyloidosis caused by serum amyloid A (SAA). The present invention makes possible the development of animal models of amyloidosis caused by other amyloidogenic proteins and for which no animal models currently exist.

In another embodiment, the invention features a method of increasing amyloid deposition in vitro. The in vitro study of amyloid fibril formation is important to the ultimate elucidation of the causes of amyloid formation in vivo. Co-pending U.S. patent application Ser. No. 08/372,178 (the disclosure of which is hereby incorporated by reference) discloses assay methods useful for studying the effects of test compounds on amyloid deposition in vitro. However, most previous studies of in vitro amyloid fibril formation have used conditions which are not similar to conditions found in vivo. For example, amyloid formation in vitro has been induced by use of concentrations of amyloidogenic proteins which are orders of magnitude greater than are found in vivo. As noted above, non-physiological pH ranges and organic solvents have also been employed to cause amyloid fibril formation. Furthermore, certain amyloidogenic proteins are resistant to fibrillogenesis in vitro, and the study of these resistant amyloidogenic proteins has heretofore been hindered by difficulties encountered in inducing fibril formation.

The use of non-physiological conditions may lead to misinterpretations. The nature of the interactions between HSPG and amyloidogenic proteins is not completely understood. Crystallographic studies of amyloid fibrils formed in vitro are a potentially powerful method of studying these interactions; however, the structure of the fibrils may be affected by the conditions used for fibril formation. For example, the structure of amyloid fibrils deposited from a solution at pH 5.6 (the pI of amyloid beta protein fragment 1-28) may not be the same as the structure of fibrils deposited at pH 7. Fibrils deposited from protein solutions of differing concentration may also not be identical. The concentration of amyloidogenic peptides found in vivo, such as serum amyloid A (SAA), varies, but may be as low as 1–5 $\mu$g/ml, under normal circumstances, to as high as about 0.5–1 mg/ml during an inflammatory reaction. For these reasons, conditions for fibril formation which more closely resemble conditions found in vivo are desirable.

The present invention provides a method of inducing amyloid fibril formation in vitro under conditions which more closely approximate physiological conditions (see Example 2). The structure of the fibrils formed in vitro by the methods provided herein is believed to more closely resemble the structure of amyloid fibrils found in subjects suffering from amyloidosis. Thus, in a preferred embodiment, the method of inducing amyloid fibril formation in vitro according to the present invention is carried out at a pH between about 6.5 and about 7.5, more preferably at a pH between about 6.2 and 7.2, and most preferably at a pH of about 7. In a preferred embodiment, the method of inducing amyloid fibril formation in vitro according to the present invention is carried in a solution which is substantially free of non-aqueous solvents. In a preferred embodiment, the method of inducing amyloid fibril formation in vitro according to the present invention is carried out on a solution of amyloidogenic peptide which has a concentration of less than about 2 mg/ml, more preferably less than about 1.5 mg/ml, and still more preferably at a concentration less than about 1 mg/ml.

An advantage of the methods according to the present invention is that the formation of amyloid fibrils is more rapid in the presence of an amyloid-enhancing compound than in the absence of the amyloid-enhancing compound. As described in Example 2, amyloid fibril formation can be a slow process, requiring up to three days. The subject methods increase the speed of amyloid formation and decrease the time necessary for fibril formation.

Interestingly, the amyloid-enhancing compounds described in Examples 1 and 2 share certain structural features in common with compounds known to decrease amyloid deposition in vivo (i.e., at least one anionic sulfonate group, see Example 1). Furthermore, the amyloid-enhancing compounds generally comprise at least one aromatic ring, with a sulfonate directly bonded to the ring. Without being bound by theory, the presence of two anionic moieties on an aromatic ring may be important for amyloid-enhancing activity.

In another aspect, the invention provides a method of screening for agents useful for treating amyloidosis. In this screening method, a combination of an amyloidogenic peptide and an amyloid-enhancing compound is provided under conditions which allow amyloid fibrils to form; a test agent is introduced into the combination forming a screening medium; and the presence or absence of amyloid fibril formation within the screening medium is detected as an indication of the ability of the test agent to treat amyloidosis. The ability of a compound to prevent amyloid deposition in vitro is related to the ability of that compound to prevent amyloid deposition in vivo (see e.g., Examples 1–3, infra).

In another aspect, the invention provides an animal or mammal having non-naturally occurring amyloid deposits, comprising an animal treated with an amyloid-enhancing compound such that the animal has non-naturally occurring amyloid deposits. Animals having non-naturally occurring amyloid deposits are useful as animal models of amyloidosis, and as such are valuable for screening compounds which are useful for treating amyloidosis. Examples of animals or mammals include mice, rats, dogs, cats, pigs, horses, primates and the like.

The invention is further illustrated by the following examples, which should not be construed as further limiting the subject invention. All references, issued patents, and patent applications cited throughout this application are incorporated herein by reference.

Exemplification

Aβ is a 40 amino acid protein associated with Alzheimer's disease. Aβ peptide was prepared and purified as described in Fraser, P. E. et al., *Biochemistry* 31, 10716 (1992). Briefly, the peptide was synthesized by standard solid-phase techniques and purified by HPLC according to well known procedures.

The sulfated and sulfonated compounds used in the examples below are commercially available (e.g. Sigma Chemical Co., St. Louis, Mo., or Aldrich Chemical Co., Milwaukee, Wis.) and/or can be synthesized by standard techniques known in the art (see, e.g., Stone, G. C. H. (1936) *J. Am. Chem. Soc.,* 58:488).

EXAMPLE 1

Swiss white mice weighing 25–30 g were given Amyloid Enhancing Factor (AEF) and AgNO$_3$ as described previously (Kisilevsky, R. and Boudreau, L. (1983) "The kinetics of amyloid deposition: I. The effect of amyloid enhancing factor and splenectomy"*Lab. Invest.,* 48, 53–59), to induce amyloidosis. Twenty four (24) hours later they were divided into groups. One group served as a control and was maintained on standard laboratory mouse chow and tap water ad lib. The test groups received standard chow but their water contained 20 or 50 mM of one of the compounds listed in Table 2, below. One compound, taurine, was tested at concentrations of 5 mM, 10 mM, 20 mM, and 50 mM. All compounds were dissolved in water containing 1.0% sucrose, and the pH adjusted to 7. Water intake was approximately equivalent for all groups. All animals were sacrificed on day six (6) of the experiment, their spleens collected, prepared for sectioning, spleen sections stained with Congo red (Puchtler, H., et al (1983) "Application of Thiazole Dyes to Amyloid under Conditions of Direct Cotton Dyeing: Correlation of Histochemical and Chemical Data" *Histochemistry,* 77, 431–445), and the percent area occupied by amyloid assessed by an image analysis apparatus and program (MCID M2, Imaging Research Inc., Brock University, St. Catherines, Ontario, Canada).

The results are summarized in Table 1, below.

TABLE 1

Effect of Sulfated and Sulfonated Compounds on AA Amyloid Deposition In vivo in Mouse Spleen

| Compound | Concentration (mM) | Amyloid Deposition* | Standard Error |
|---|---|---|---|
| 1,5-Pentanedisulfonate† | 50 | 76 | 11 |
|  | 20 | 60 | 20 |
| 1,6-Hexanedisulfonate† | 50 | 117 | 17 |
|  | 20 | 98 | 26 |

TABLE 1-continued

Effect of Sulfated and Sulfonated Compounds on AA Amyloid Deposition In vivo in Mouse Spleen

| Compound | Concentration (mM) | Amyloid Deposition* | Standard Error |
|---|---|---|---|
| 1,2-Ethanediol disulfate† | 50 | 8 | 2 |
|  | 20 | 36 | 10 |
| 1,3-Propanediol disulfate† | 50 | 11 | 4 |
|  | 20 | 32 | 11 |
| 1,4-Butanediol disulfate† | 50 | 54 | 22 |
|  | 20 | 44 | 11 |
| Taurine | 50 | 68 | 15 |
|  | 20 | 45 | 23 |
|  | 10 | 34 | 16 |
|  | 5 | 95 | 33 |
| WAS-10 | 50 | 79 | 22 |
|  | 20 | 80 | 23 |
| WAS-11 | 50 | 114 |  |
|  | 20 | 114 |  |
| WAS-12 | 50 | 55 |  |
|  | 20 | 74 |  |
| WAS-13 | 50 | 81 |  |
|  | 20 | 63 |  |
| WAS-14 | 50 | 135 | 27 |
|  | 20 | 83 | 28 |
| WAS-15 | 50 | 56 | 13 |
|  | 20 | 102 | 24 |
| WAS-16 | 50 | 48 | 12 |
|  | 20 | 98 | 30 |
| WAS-17 | 50 | 60 | 21 |
|  | 20 | 54 | 31 |
| WAS-18 | 50 | 110 | 35 |
|  | 20 | 97 | 50 |
| WAS-19 | 50 | 61 | 13 |
|  | 20 | 117 | 28 |
| WAS-20 | 50 | 192 | 37 |
|  | 20 | 119 | 19 |
| WAS-21 | 50 | 158 | 19 |
|  | 20 | 130 | 28 |
| WAS-22 | 50 | 83 | 19 |
|  | 20 | 155 | 28 |
| WAS-23 | 50 | 66 | 12 |
|  | 20 | 94 | 11 |
| WAS-24 | 50 | 103 | 19 |
|  | 20 | 110 | 15 |
| WAS-27 | 50 | 100 | 18 |
|  | 20 | 86 | 30 |
| WAS-28 | 50 | 56 |  |
|  | 20 | 53 |  |
| WAS-34 | 50 | 53 |  |
|  | 20 | 59 |  |
| WAS-35 | 50 | 51 |  |
| WAS-36 | 50 | 71 |  |
| WAS-37 | 50 | 100 |  |
|  | 20 | 102 |  |
| WAS-38 | 50 | 81 |  |

†As the sodium salt.
*Amyloid deposition is given as a percentage of untreated control. All measurements are the average of 3–5 animals.

The results indicate that animals treated with sodium 1,2-ethanediol disulfate or sodium 1,3-propanediol disulfate had at least about a 65% decrease in amyloid deposition at 20 mM and at least about a 90% decrease in amyloid deposition at 50 mM. Animals treated with sodium 1,4-butanediol disulfate (50 mM), sodium 1,5-pentanedisulfonate ((50 mM), taurine (sodium 2-aminoethanesulfonate) (10–20 mM), 3-(cyclohexylamino)-1-propanesulfonate (WAS-12) (50 mM), 4-(2-hydroxyethyl)-1-piperazineethanesulfonate (WAS-13) (20 mM), 3-(N-morpholino)propanesulfonic acid (MOPS) (WAS-15) or its sodium salt (WAS-16) (50 mM), sodium tetrahydro-3,4-thiophene-1,1-dioxide-3,4-disulfonate trihydrate (WAS-19), sodium 4-hydroxybutane-1-sulfonate (WAS-17) (50 mM), sodium 1,3,5-pentanetriol trisulfate (WAS-28) (20 and 50 mM), 2-aminoethyl hydrogen sulfate (WAS-34) (20 and 50 mM), Indigo Carmine (WAS-35) (50 mM) had at least approximately a 40% decrease in amyloid deposition compared to untreated control animals. Taurine caused decreased amyloid deposition at concentrations of 10–20 mM, but had less effect at 5 mM or 50 mM.

The results indicate that certain compounds increased the amount of amyloid deposition in vivo. Administration of 4,5-dihydroxy-1,3-benzenedisulfonic acid (WAS-21) or 2,5-dihydroxy-1,4-benzenedisulfonic acid (WAS-20) resulted in increased levels of splenic amyloid. Without wishing to be bound by theory, it is believed that two aromatic sulfonate moieties are important to the amyloid-enhancing activity of the subject compounds (see below).

EXAMPLE 2

Samples of amyloid were prepared for electron micrographic (EM) examination as described in Kisilevsky et al. *Nature Med* (1995), loc. cit.. Briefly, negatively-stained fibrils of Aβ were prepared by floating pioloform carbon-coated grids on peptide solutions (1–2 mg/ml, 20 mM Tris-HCl, pH 7) that had been preincubated for 72 hours at 37° C. to ensure extensive Aβ polymerization. A control sample contained no test compound. Test compounds were added at ten-fold molar excess to preformed amyloid fibrils with a subsequent incubation for 24 hours at 37° C. After the grids were blotted and air-dried, the samples were stained with 1% phosphotungstic acid (w/v) and visualized on a Hitachi H-7000 electron microscope operated at 75 kV. Fibril dimensions were calibrated using tropomyosin paracrystals.

Aβ fibrils were generated and then treated with WAS-6 (1,3-propanediol disulfate, sodium salt). The fibrils treated with WAS-6 showed a marked reduction in numbers, attenuation in length, and had a much coarser appearance than the control fibrils. Thus, WAS-6 can be classified as an amyloid inhibitor.

Amyloid fibrils were then generated and treated with WAS-20 (2,5-dihydroxy-1,4-benzenedisulfonic acid). EM examination of the fibrils formed showed increased amounts of fine fibrils, compared to the control sample. Thus, WAS-20 can be classified as an amyloid enhancer in vitro. In a similar experiment, WAS-21 was classified as an amyloid enhancer in vitro. These results are consistent with the in vivo assay performed in Example 1, supra. WAS-46 (2,5-dimethoxy-1,4-benzenedisulfonic acid), a methylated derivative of WAS-20, was also found to be an amyloid enhancer in vitro. This result demonstrates that a free phenolic hydroxyl group is not necessary for amyloid enhancing activity.

Amyloid fibrils were then generated and treated with WAS-52 (4-amino-3-hydroxy-1-naphthalenesulfonic acid) or WAS-53 (3,4-diamino-1-naphthalenesulfonic acid. EM examination of the fibrils formed showed no increase in number of fibrils compared to a control sample. Thus, WAS-52 and WAS-53 are not amyloid enhancers in vitro.

EXAMPLE 3

β-pleated sheet secondary structure is characteristic of all amyloid deposits, so destabilization of β-sheet formation may reduce the rate of amyloid deposition; conversely, compounds which increase β-sheet formation may increase the rate of amyloid deposition. Determination of amyloid protein conformation by CD has been reported (McCubbin, W. D. et al., *Biochem J*. 256, 775 (1988)); the amount of β-sheet present in a sample was related to the minimum at about 218 nm.

All CD experiments were performed on a Jasco J-720 instrument. The cell was maintained at 25° C. using a circulating water bath. Computer-averaging of traces was performed to improve signal-to-noise ratios. The solvent signal was subtracted.

CD experiments were performed for each test compound according to the following procedure:

A stock solution of purified peptide was made by dissolving the peptide in phosphate-buffered saline (PBS) to a concentration of 2 mg/ml. A test solution was made for each potential therapeutic agent (test compound) as shown below:

| | |
|---|---|
| Aβ stock solution | 25 μl |
| Test compound (20 mg/ml) | 2.5 μl |
| Distilled water | 2.5 μl |
| 10 mM Tris buffer, pH 7 | 370 μl |

The control sample had no test compound, and a total of 5 μl distilled water was added. The test solution was incubated for either 0 or 24 hours at 37° C. before CD measurement.

Figure 2:
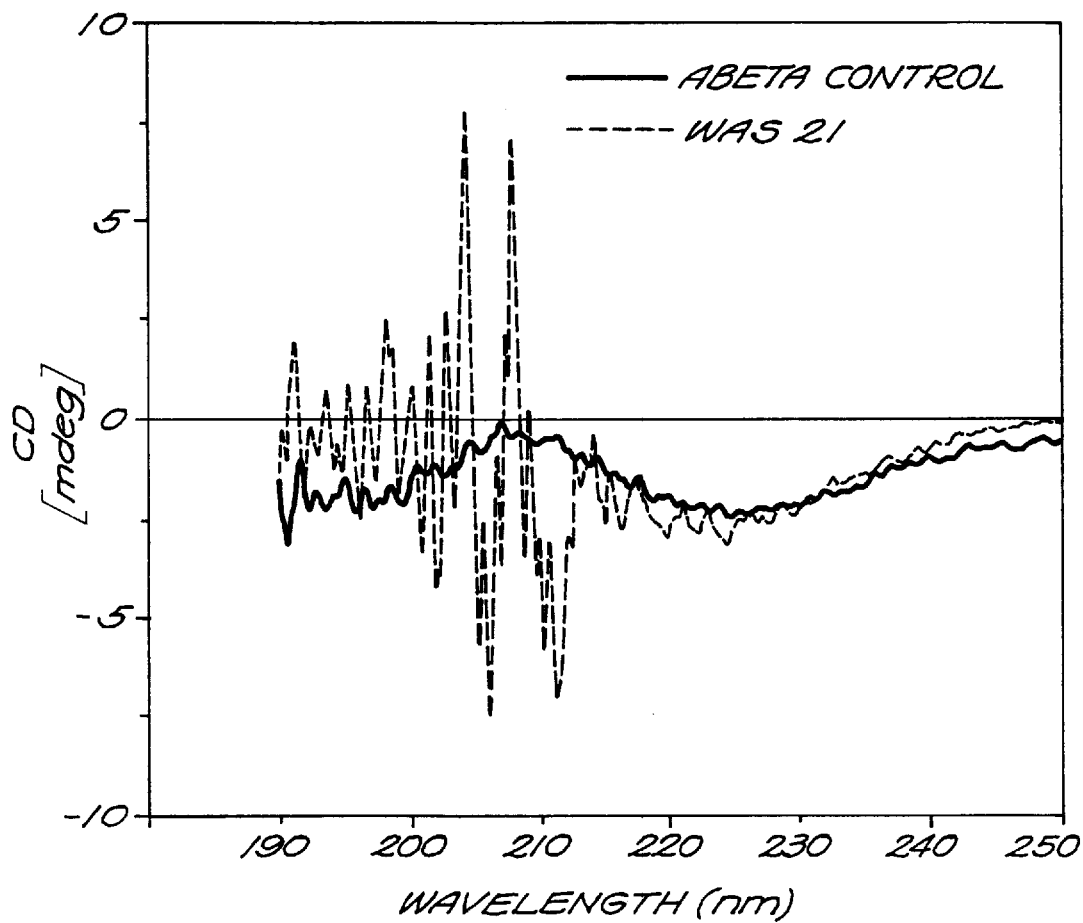
FIG. 2 shows circular dichroism (CD) spectra of Aβ in the absence and presence of WAS-21 (4,5-dihydroxy-1,3-benzenedisulfonic acid).

FIG. 1 shows the CD spectrum of Aβ in the presence and the absence of compound WAS-20 (2,5-dihydroxy-1,4-benzenedisulfonic acid). The spectra show the effect of WAS-20 on the secondary structure of the amyloid peptide. The size of the minimum near 218 nm is diagnostic of the presence of β-pleated sheet. The amount of β-pleated sheet by this measurement is about 20% greater in the presence of WAS-20; as previously noted, compounds which increase β-sheet formation may increase the rate of amyloid deposition. WAS-20 also increases the amount of light-scattering from the sample, as evidenced by the greatly increased noise at shorter wavelengths; this scattering is believed to be the result of larger aggregated particles produced by the test compound. Thus, WAS-20 can be classified as an amyloid enhancer by this in vitro assay. Similar results were obtained with WAS-21 (4,5-dihydroxy-1,3-benzenedisulfonic acid), as shown in FIG. 2. Although the change in the minimum near 218 nm is not as large for WAS-21 as for WAS-20, the increased light-scattering due to larger aggregated particles is evident. These results are consistent with the in vivo and in vitro assays performed in Examples 1 and 2, supra.

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method of forming amyloid fibrils in vitro from an amyloidogenic peptide, comprising contacting an amyloidogenic peptide with an effective amount of an amyloid-enhancing compound comprising an aromatic moiety and at least two anionic moieties selected from the group consisting of 2-sulfobenzoic acid, benzene-1,2-disulfonic acid, benzene-1,3-disulfonic acid, benzene-1,4-disulfonic acid, 4,5-dihydroxy-1,3-benzenedisulfonic acid, 2,5-dihydroxy-1, 4-benzenedisulfonic acid, 2,5-dimethoxy-1,4-benzenedisulfonic acid, and pharmaceutically acceptable salts thereof, so that amyloid fibrils are formed.

2. The method of claim 1, wherein the amyloidogenic peptide is in solution.

3. An in vitro method of screening for agents potentially useful for treating amyloidosis, comprising providing a combination of an amyloidogenic peptide and an amyloid-enhancing compound comprising an aromatic moiety and at lease two anionic moieties selected from the group consisting of 2-sulfobenzoic acid, benzene-1,2-disulfonic acid, benzene-1,3-disulfonic acid, benzene-1,4-disulfonic acid, 4,5-dihydroxy-1,3-benzenedisulfonic acid, 2,5-dihydroxy-1,4-benzenedisulfonic acid, 2,5-dimethoxy-1,4-benzenedisulfonic acid, and pharmaceutically acceptable salts thereof, under conditions which allow amyloid fibrils to form;

introducing a test agent into the combination forming a screening medium; and detecting the presence or absence of amyloid fibril formation within the screening medium as an indication of the ability of the test agent to potentially treat amyloidosis.

4. A method of increasing amyloid deposition in a non-human mammal, comprising administering to the mammal, under conditions under which amyloid deposits can form, an effective amount of an amyloid-enhancing compound comprising an aromatic moiety and at least two anionic moieties selected from the group consisting of 2-sulfobenzoic acid, benzene-1,2-disulfonic acid, benzene-1,3-disulfonic acid, benzene-1,4-disulfonic acid4,5-dihydroxy-1,3-benzenedisulfonic acid, 2,5-dihydroxy-1,4-benzenedisulfonic acid, 2,5-dimethoxy-1,4-benzenedisulfonic acid, and pharmaceutically acceptable salts thereof, such that an increase of amyloid deposition occurs in the mammal compared to amyloid deposition in the mammal in the absence of the compound, wherein the compound alters an interaction between a constituent of basement membrane and an amyloidogenic protein, or the compound alters an interaction between monomers of an amyloidogenic protein.

5. A method of increasing amyloid deposition in a non-human mammal in which amyloidosis has been induced, comprising admimistering to the mammal an effective amount of an amyloid-enhancing compound comprising an aromatic moiety and at least two anionic moieties selected from the group consisting of 2-sulfobenzoic acid, benzene-1,2-disulfonic acid, benzene-1,3-disulfonic acid, benzene-1,4-disulfonic acid, 4,5-dihydroxy-1,3-benzenedisulfonic acid, 2,5-dihydroxy-1,4-benzenedisulfonic acid, 2,5-dimethoxy-1,4-benzenedisulfonic acid, and pharmaceutically acceptable salts thereof, such that a increase of amyloid deposition occurs in the mammal in which amyloidosis has been induced in excess of amyloid deposition in the absence of said amyloid-enhancing compound.

* * * * *